United States Patent [19]

Onoda et al.

[11] 4,018,816
[45] Apr. 19, 1977

[54] PREPARATION OF METHACRYLATES

[75] Inventors: Takeru Onoda, Yokohama; Masayuki Otake, Tokyo, both of Japan

[73] Assignee: Mitsubishi Chemical Industries Ltd., Tokyo, Japan

[22] Filed: Dec. 17, 1975

[21] Appl. No.: 641,824

[30]    Foreign Application Priority Data

Dec. 19, 1974   Japan ............................ 49-146617
May 19, 1975   Japan .............................. 50-59441

[52] U.S. Cl. ............................ 260/486 R; 252/424
[51] Int. Cl.² ........................................ C07C 69/54
[58] Field of Search ................................ 260/486 R

[56]    References Cited

UNITED STATES PATENTS 3,639,461   2/1972   Ito et al. ........................ 260/486 R

*Primary Examiner*—Paul J. Killos
*Attorney, Agent, or Firm*—Lane, Aitken, Dunner & Ziems

[57]    ABSTRACT

A methacrylate is prepared by reacting methacrylic acid and an alcohol in vapor phase in the presence of a catalyst. The catalyst is a solid acid catalyst of silica-titania obtained by coprecipitating the same from an aqueous solution of a silicon and a titanium compound.

17 Claims, No Drawings

PREPARATION OF METHACRYLATES

BACKGROUND OF INVENTION 1. a. Field of Invention

This invention relates to the preparation of a methacrylate, and more particularly to a process for the preparation of a methacrylate by reacting methacrylic acid and an alcohol in vapor phase in the presence of a catalyst.

2. b. Description of the Prior Art

Methacrylates have been commercially prepared by reacting acetone cyanohydrin and sulfuric acid to form methacrylamide sulfate and then adding water and an alcohol to effect hydrolysis and esterification.

In the prior art, it is known to react methacrylic acid and alcohols at elevated temperatures in liquid or vapor phase in the presence of various catalysts. However, these methods have not been satisfactory due to the high polymerizability of the starting material and the product and difficulties in the separation and the purification of products. In consideration of the fact that starting material and product are highly polymerizable, the esterification should be carried out under the mildest conditions and completed within the shortest possible period of time. Therefore it is advantageous to carry out the reaction in vapor phase for a short contact time by employing a highly active catalyst.

A number of catalysts for the esterification of methacrylic acid in vapor phase have been proposed as listed below.

a. Silica gel catalyst (Japanese Patent Publication No. 17706/1961)
b. Phosphoric acid - diatomaceous earth catalyst (Japanese Patent Publication No. 5222/1967)
c. Silica-alumina catalyst (Japanese Patent Publication No. 6324/1967)
d. Molybdenum oxide, molybdenum sulfide and sulfided cobalt-molybdate catalysts (Japanese Patent Publication No. 4332/1969)
e. Molybdenum sulfide catalyst (Japanese Patent Publication No. 9885/1969)
f. Titanium oxide-antimony oxide-silica catalyst (Japanese Patent Publication No. 24564/1970)
g. Sulfuric acid- or sulfonic acid-carrying catalyst (U.S. Pat. No. 3,392,191)
h. $TiO_2$, $TiO_2$-$Sb_2O_5$, $TiO_2$-$SiO_2$ and $TiO_2$-$Sb_2O_5$-$SiO_2$ catalysts (U.S. Pat. No. 3,639,461)

The above-listed catalysts, however, have disadvantages in that elevated temperatures are required for the reaction due to their low activity and the products can not be readily separated and purified due to low conversion and so on. In a prior art process where low selectivity of methacrylate requires the presence of water vapor in the reaction gas, the separation and purification of the product is difficult. Moreover, some catalysts are unstable and their initial activity disappears after a short period of time and thus are not suitable for industrial use.

SUMMARY OF INVENTION

It has now been discovered that the above-described disadvantages of the prior art processes can be obviated and the yield of methacrylate increased by a vapor phase reaction using a solid acid catalyst of a silica-titania prepared by coprecipitation.

One aspect of the invention is the provision of a process for the preparation of a methacrylate by contacting methacrylic acid with an alcohol in vapor phase at elevated temperatures in the presence of a specific catalyst. A solid acid catalyst of silica-titania is prepared by dissolving a silicon and a titanium compound in an aqueous medium, adjusting the pH of the resultant aqueous solution so as to coprecipitate the silicon and the tetanium components and then drying and calcining the coprecipitate. This catalyst can be used to form methacrylates in extremely high yields.

In one embodiment of the invention, a hydroxylbearing organic compound having a molecular weight of more than 300 is dispersed in the aqueous solution of the silicon and the titanium compounds before coprecipitation. The thus obtained solid acid catalyst of silica-titania having a high activity also used as the catalyst for the esterification, ensuring the formation of the methacrylate in high yields.

DETAILED DESCRIPTION OF INVENTION

The solid acid catalyst of silica-titania of the present invention is prepared as follows.

Examples of the silicon compounds which may be used as the raw material for the silicon component include silicon halides such as silicon tetrachloride, silicate salts such as sodium silicate, silicate esters such as ethyl orthosilicate and the like.

Examples of the titanium compounds which may be used as the raw material for the titanium component include titanium halides such as titanium tetrachloride, titanium salts of inorganic acids such as titanium sulfate, titanate esters such as orthotitanates and the like.

As a precipitation aid for the coprecipitation of the silicon and the titanium components is used a hydroxylbearing organic compound having a molecular weight of more than 300. Examples of such organic compounds include polysaccharides such as starch, crystalline cellulose, pulp, maltose, saccharose, etc., polysaccharide derivatives such as methyl cellulose, carboxymethyl cellulose, acetyl cellulose, etc., polyacetals such as paraformaldehyde, etc., polyalkylene glycols such as polyethylene glycol, polypropylene glycol, etc., polymers of unsaturated alcohols such as polyvinyl alcohol, ethylene-vinyl alcohol copolymers, etc., and the like. The term "crystalline cellulose" means an insoluble residue which is obtained by treating ordinary cellulose with an acid or an alkali to decompose the non-crystalline portion thereof. When solid precipitation additives are used, it is preferred to use them in the form of fine particles in order to achieve a uniform dispersion thereof in the aqueous solution.

Particularly suitable among the above-described precipitation additives are starch, crystalline cellulose, methyl cellulose, polyethylene glycol having a molecular weight of more than 400 (generally less than $10^7$) and polyvinyl alcohol having a molecular weight of more than 500 (generally less than $10^7$).

According to the process of this invention the above-described silicon and titanium compounds are first dissolved in a suitable aqueous medium to form an aqueous solution. To this end the silicon and titanium compounds may be simultaneously or successively added to the aqueous medium, or aqueous solutions of the silicon and the titanium compounds may be formed respectively and then combined.

Examples of the aqueous mediums used for preparing the aqueous solution include water, a solution of a mineral acid in water, a solution of an alkali in water, a solution of an alcohol in water and the like. Even if the aqueous medium used is neutral, the aqueous solution of the silicon and the titanium compounds may be acidic or basic depending on properties of the silicon and the titanium compounds. For example, silicon tetrachloride and titanium tetrachloride, both of which are hydrolyzed to give hydrochloric acid, are acidic, while sodium silicate is basic. Thus the aqueous solution of such a compound may be acidic or basic.

The ratio of the silicon to the titanium compounds used in accordance with the invention can vary over a wide range. It is preferable to use the silicon and the titanium compounds in such proportions that the ratio of silicon to titanium atoms in the aqueous solution (Si/Ti) falls generally in the range of 0.1 – 100, preferably in the range of 0.2 – 20.

When the above-described precipitation additive is used, the same can be added at any desirable stage during the preparation of the aqueous solution of the silicon and the titanium compounds. For example, the silicon and the titanium compounds are first dissolved in the aqueous medium, then with stirring the precipitation additive is added to this aqueous solution to disperse the additive therein. The precipitation additive may be dispered in the aqueous solution in the form of either colloidal or coarse dispersions or by dissolution. The precipitation additive can be added normally in an amount of 1 – 100 wt%, preferably 2 – 20 wt% on the basis of the solid silica-titania calculated on the assumption that all the silicon and the titanium compounds used as starting materials are converted into $SiO_2$ and $TiO_2$, respectively.

In accordance with the invention the silicon and the titanium components are coprecipitated by adjusting the pH of the aqueous solution containing the silicon and the titanium compounds and by adding a precipitation aid, if desired. To this end a basic or an acidic substance is added to the aqueous solution with stirring. For example, to an acidic aqueous solution obtained by dissolving the silicon and the titanium compounds in an acidic aqueous medium may be added an alkaline solution of an alkali hydroxide, an alkali carbonate or the like, a solution of urea in water, ammonia water or a buffer solution thereof. Adjustment of the aqueous solution to approximately pH 7 is preferred to initiate the coprecipitation, which is carried out normally at a temperature of 0° – 80° C, preferably 10° – 60° C. The coprecipitation time depends on the properties of the pH-adjusting additive. With the use of inorganic compounds the coprecipitation will be complete in shorter periods of time, while with urea it takes longer periods of, on the order of one day.

The resultant coprecipitate containing the silicon and the titanium components is subjected to the following successive treatments:
1. aging for about 1 to 30 hours,
2. separating from the mother liquor by filtration, decantation, etc.,
3. washing in a conventional manner with water or an aqueous solution containing ammonium ions such as ammonia water, a solution of ammonium chloride or nitrate in water, a buffer solution of ammonia and ammonium chloride or nitrate and the like.
4. drying, and
5. calcining at an elevated temperature in the range of 250° to 1200° C, preferably 250° to 1100° C, and more preferably 350° to 950° C, for 1 to 100 hours in the flow of air or oxygen gas.

These treatments can provide a silica-titania useful as a solid acid catalyst for the process of this invention. If a precipitation additive is used for the coprecipitation, the calcining is continued until the additive has been completely burned off.

The resultant solid acid catalyst of silica-titania may be used in the form of powder, if desired, after being sifted with a screen, in the process of the invention. In most cases it is preferred to mold the solid silica-titania. The molding can be carried out after the above-described drying or calcining.

Since the solid acid catalyst is prepared by the coprecipitation in accordance with the invention, it is essentially different from a conventional carrier-type catalyst, which is a catalyst prepared from two components one of which is a solid and the other is a soluble compound, the latter or a decomposed product thereof being carried on the former. With respect to solid acid catalyst of silica-titania according to the invention it has been found that the acidity of the solid acid catalyst (hereafter referred to as the solid acidity) is considerably increased, since the silicon and the titanium components are intimately and homogeneously dispersed in the solid and consequently interact with each other to a remarkable extent. It has been found by experimental measurements that the catalyst of this invention has a solid acid strength (pKa value) of $-8.2$ to $-5.6$ over the above-described wide range of the atomic ratio of silicon to titanium. On the other hand, the carrier-type silicatitania catalyst which is prepared, for example, by impregnating silica with an aqueous solution of titanium tetrachloride and then hydrolyzing the impregnated titanium tetrachloride has a pKa value of the order of $-3.0$, which indicates the superiority of the catalyst of this invention in terms of the solid acidity.

It is to be noted that the addition of a precipitation additive as described above can further increase the activity of the catalyst. In the prior art, it is known to mold powdered catalysts or carrier materials with the addition of a water-soluble high polymer such as methyl cellulose, polyethylene glycol, polyvinyl alcohol, etc. in order to improve the moldability. Japanese Patent Publication No. 28598/1972 discloses a process wherein an insoluble solid having a grain size within a certain limit, for example, crystalline cellulose, etc. is added to a catalyst base and molded product is sufficiently calcined to burn off the added solid, yielding a product with micropores having a diameter distribution in the range of 3,000 to 5,000 angstrom. In contrast to the effect of the above-described molding additive and the surface treatment agent, the precipitation additive according to this invention serves to improve the dispersion of silicon and titanium components during the coprecipitation. For example, if the precipitation additive used is water-soluble, a part or a large part of the additive remains in the aqueous solution after the separation or is entrained in water during the washing so that only a comparatively small part of the additive is present in the resultant product but shows a marked improvement upon the catalystic activity of the product. The distribution of micropores shows no noticeable change whether the precipitation additive is used or not.

In accordance with the invention methacrylic acid is reacted with an alcohol in vapor phase in the presence of the above-described solid acid catalyst of silica-titania, yielding a methacrylate with high conversion and selectivity.

An aliphatic alcohol having 1 to 4 carbon atoms and 1 to 2 hydroxyl groups is used as the alcohol reacted with the methacrylic acid. Specific examples of such an alcohol include methanol, ethanol, propanol, 2-propanol, butanol, isobutyl alcohol, ethylene glycol, propylene glycol, butanediol, allyl alcohol, etc.

The catalyst may be used in the form of a fixed bed, a moving bed or a fluidized bed. A fixed bed is preferred.

The molar ratio of alcohol to methacrylic acid lies in the range of 0.5 – 100, preferably 1 – 20.

The reagents, the alcohol and methacrylic acid, may be directly esterified or they may be diluted with a gas which is virtually inert to the reaction, for example, nitrogen, air, carbon dioxide, etc. before they are subjected to esterification. Since the catalyst of this invention has sufficiently high selectivity, the esterification does not require the addition of water. Instead, it is preferred to use reagents in which water contents are as small as possible.

The esterification is carried out at a temperature of 160° – 360° C, preferably 160° – 300° C. The space velocity lies in the range of 100– 100,000 hr$^{-1}$, preferably 1,000 – 10,000 hr$^{-1}$. The resultant gas is condensed and the methacrylate is then separated from the condensate in a conventional manner by extraction, distillation, etc.

The catalyst of this invention is stable and can maintain its high activity for relatively longer periods of time. If the catalyst has lost its activity to some extent, it can readily be regenerated by calcining the same in the presence of a molecular oxygen-containing gas such as air under the same conditions as those for its preparation.

Thus, the catalyst of this invention is highly valuable for commercial use because it possesses high activity and selectivity and produces methacrylate in high yields at comparatively low temperatures.

EXAMPLE

A. Preparation of Catalyst

Catalyst - A1

Into 50 ml of diluted hydrochloric acid cooled with ice water was poured and dissolved 16.8 g of titanium tetrachloride and then 200 ml of water was added thereto. To this solution cooled with ice water was added dropwise 59 g of silicon tetrachloride. After the addition had been completed, with vigorous stirring to the resultant solution was added dilute ammonia water (obtained by diluting 28% ammonia water with the same volume of water) in a sufficient amount to adjust the pH of the solution to 7.0. This pH-adjusted solution was heated at a temperature of 60° C for two hours with continuous stirring and then allowed to stand overnight. The resultant precipitate was filtered, washed, dried at 100° C and then calcined at 400° C in a flow of air. The calcined product was sifted with screens and particles within the range of 16 – 60 mesh (Tyler) were collected. The resultant solid acid catalyst of silica-titania had an atomic ratio of silicon to titanium (Si/Ti) of 4 and a specific surface area of 165 m$^2$/g. The solid product calcined at 400° C was tested for its solid acid strength with the Hammett indicator, showing a pKa = −8.2.

Catalyst - A2

In 100 ml of ethanol-water (volume ratio = 4 : 1) was dissolved 26.0 g of ethyl orthosilicate. 23.7 g of titanium tetrachloride was gradually added to water cooled with ice to form a homogeneous solution. After the above-described two solutions had been combined, with vigorous stirring the mixed solution was neutralized with a suitable amount of dilute ammonia water (obtained by diluting 28% ammonia water with a five-fold volume of water) and an additional 800-ml portion of water, adjusting to pH 7.0. This solution was stirred an additional two hours and then allowed to stand overnight. The resultant precipitate was filtered, washed, dried and then calcined at 400° C in a flow of air. The calcined product was sifted with screens to obtain the catalyst particles. The resultant solid acid catalyst of silica-titania had an atomic ratio of Si/Ti = 1 and a specific surface area of 320 m$^2$/g. Determination of the solid acid strength by titration with the Hammett indicator showed pKa = −8.2.

Catalyst - C1

Silica (manufactured by Fuji-Davison Co., specific surface area 380 m$^2$/g) was sifted with screens and a 9.0 g portion of these particles within the range of 30 – 60 mesh (Tyler) was used. The silica particles were dipped in a solution of 2.38 g of titanium tetrachloride in 15.0 ml of cold water. This impregnated silica was dried at 100° C in a water bath and then subjected to hydrolysis. The resultant product was heated at 80° – 150° C for one hour in a tube made of quartz through which air saturated with water vapor at 60° C was passed. Thereafter the product was further calcined at 400° C in dry air, to obtain the titanium dioxide (TiO$_2$)-carrying catalyst. It was found that the amount of titanium dioxide in the catalyst was 10 wt% and the specific surface area was 250 m$^2$/g. Determination of the solid acid strength by titration with the Hammett indicator showed pKa = −3.0.

Catalyst - C2

Titanium tetrachloride was hydrolyzed in water. The hydrolyzed product was filtered, washed, dried and calcined as in the preparation of catalyst - A1, yielding a titanium dioxide (TiO$_2$) catalyst which had no carrier. This catalyst had a specific surface area of 25 m$^2$/g.

Catalyst - A3

A 25 g portion of 40% titanium sulfate solution of commercial grade (containing a 30% excess of sulfuric acid) was added to a solution of 28.5 g of sodium silicate solution of commercial grade (containing 35 – 38% of SiO$_2$ and 17 – 19% of Na$_2$O) in 500 ml of water. The resultant solution had a pH of less than 1. To this solution was added a suitable amount of 28% ammonia water to adjust its pH to 7.5 and then the solution was allowed to stand overnight. The resultant coprecipitate was filtered and washed with 0.1% ammonium chloride solution, dried at 100° C and then calcined at 400° C for two hours in air. It was found that the calcined product had an atomic ratio of Si/Ti = 4 and a specific surface area comparable with that of Catalyst - A1.

Catalyst - B1

To 500 ml of an aqueous solution containing 10.0 g of 40 wt% titanium sulfate solution acidified with sulfuric acid and 25.7 g of 30 wt% water-glass solution in water was added 5 g of microcrystalline cellulose powder. With stirring to this solution was added 20 ml of dilute ammonia water (obtained by diluting 28% ammonia water with a five-fold volume of water), adjusting its pH to 7.0. This solution was aged for a while by heating and then allowed to stand overnight. The resultant coprecipitate was washed with a buffer solution of NH$_4$OH - NH$_4$Cl (pH 7.5), dried and then calcined at 400° C in flow of air. There was obtained a calcined product having an atomic ratio of Si/Ti = 9, suitable for use as catalyst.

Catalyst - A4

The procedures described in the preparation of Catalyst - B1 were repeated except that the cellulose powder was not added. There was obtained a calcined product having an atomic ratio of Si/Ti = 9.

Catalyst - C3

A mixture of 4.00 g of titanium dioxide obtained by hydrolyzing titanium tetrachloride, 27.0 g of commercial silicon dioxide (manufactured by Fuji-Davison Co.) and 1.55 g of crystalline cellulose powder was thoroughly kneaded in a ball mill and then molded into tablets of 5 mm (diameter) × 2 mm (thickness) by means of a tablet machine. These tablets were calcined at 450° C in a flow of oxygen, yielding a catalyst having an atomic ratio of Si/Ti = 9.

Catalyst - A5

A mixture of 5.0 g of Catalyst -A4 and 0.25 g of crystalline cellulose powder was thoroughly kneaded in a ball mill and then molded and calcined in accordance with the procedures described in the preparation of Catalyst - C3. There was obtained a catalyst having an atomic ratio of Si/Ti = 9.

Catalyst - B2

To 500 ml of an aqueous solution which contained 43.7 g of 40 wt% titanium sulfate solution acidified with sulfuric acid and 50.0 g of 30 wt% water-glass solution in water was added 10 g of methyl cellulose (manufactured and sold by Wako Junyaku Co. under the trademark of "CP400"). This solution was subjected to the procedures described in the preparation of Catalyst - B1. There was obtained a calcined product having an atomic ratio of Si/Ti = 4.

Catalyst - B3

The procedures described in the preparation of Catalyst - B2 were repeated except that 5 g of polyethylene glycol (manufactured and sold by Kishida Chemical Co. under the trademark of "PEG-4000", average polymerization degree 4000) was used in place of the methyl cellulose. There was obtained a catalyst having an atomic ratio of Si/Ti = 4.

Catalyst - B4

The procedures described in the preparation of Catalyst - B2 were repeated except that 5 g of polyvinyl alcohol (manufactured and sold by Wako Junyaku Co. under the trademark of "PVA-2000", average polymerization degree 2000) was used in place of the methyl cellulose. There was obtained a catalyst having an atomic ratio of Si/Ti = 4.

Catalyst - A6

The procedures described in the preparation of Catalyst - B2 were repeated except that the methyl cellulose was omitted. There was obtained a catalyst having an atomic ratio of Si/Ti = 4.

Catalyst - A7

The procedures described in the preparation of Catalyst - B2 were repeated except that 10 g of polymethyl methacrylate powder (fine particles of more than 100 mesh (Tyler) manufactured by Yoneyama Yakuhin Kogyo Co.) was used in place of the methyl cellulose. There was obtained a catalyst having an atomic ratio of Si/Ti = 4.

Catalyst - B5

The procedures described in the preparation of Catalyst - B1 were repeated except that the calcining was carried out at 650° C.

Catalyst - B6

The procedures described in the preparation of Catalyst - B1 were repeated except that the calcining was carried out at 800° C.

B. Esterification

Run 1

Into a reaction vessel made of hard glass was placed 1.6 ml of Catalyst - A1 and then a mixture of methanol and methacrylic acid (molar ratio = 4 : 1) was introduced through a microfeeder, with nitrogen gas as a carrier gas. The reaction was carried out at a temperature of 220° C for a contact time of 0.5 sec. The reaction product was collected in a methyl cellosolve-water (1:1) solution. Analyses by acid titration and gas chromatography showed the per-pass yield of methyl methacrylate (MMA) to be 97.1% and the selectivity to be nearly 100%. Hardly any dimethyl ether formed by the dehydration of methanol was detected.

Run 2

Run 1 was repeated except that the reaction temperature was lowered to 200° C. It was found that the conversion of methacrylic acid was 98.6% and the per-pass yield of MMA was 97.0%. More than 98% of methanol was recovered as a total of the MMA product and the unreacted methanol.

Run 3

In the presence of Catalyst - B1 ethylene glycol and methacrylic acid were subjected to esterification in vapor phase under the following conditions:

| Feed rate | ethylene glycol | 86.19 m.mol/hr |
|---|---|---|
| | methacrylic acid | 40.55 m.mol/hr |
| | nitrogen gas | 156.15 m.mol/hr |
| Amount of catalyst used | | 1.0 ml |
| Contact time | | 0.568 sec |
| Reaction temperature | | 200 – 320° C |
| Reaction pressure | | atmospheric pressure |

The products were weighed. The results are shown in Table 1.

Table 1

| Reaction Temperature | Amount of β-hydroxyethyl methacrylate produced | Amount of unreacted ethylene glycol | Amount of unreacted methacrylic acid |
|---|---|---|---|
| 210° C | 3.71 m.mol/hr | 82.48 m.mol/hr | 36.84 m.mol/hr |
| 310° C | 25.84 " | 49.00 " | 14.71 " |

Runs 4 – 17

In the presence of different catalysts methanol and methacrylic acid were continuously subjected to esterification in vapor phase at a temperature of 200° C under atmospheric pressure. The molar ratio of methanol to methacrylic acid in the feed was 4 : 1. The activities of the respective catalysts were compared in terms of the rate constant k of reaction calculated from the following rate equation:

$$\frac{d[MMA]}{dt} = k \cdot P_A \cdot P_M$$

MMA : methyl methacrylate
$P_A$ : partial pressure of methacrylic acid
$P_M$ : partial pressure of methanol Values of the rate constant $k$ corresponding to the respective catalysts are shown in Table 2. Runs 17 – 19 in Table 2 are comparative examples.

Table 2

| Run No. | Catalyst | k (hr$^{-1}$) |
|---|---|---|
| 4 | A1 | 22,700 |
| 5 | A2 | 30,460 |
| 6 | A3 | 18,500 |
| 7 | A4 | 28,000 |
| 8 | A5 | 30,000 |
| 9 | A6 | 29,000 |
| 10 | A7 | 12,500 |
| 11 | B1 | 100,300 |
| 12 | B2 | 53,000 |
| 13 | B3 | 56,800 |
| 14 | B4 | 68,500 |
| 15 | B5 | 120,000 |
| 16 | B6 | 142,000 |
| 17 | C1 | 6,600 |
| 18 | C2 | 290 |
| 19 | C3 | 750 |

What is claimed is:

1. In a process for the preparation of a methacrylate by the vapor phase reaction of methacrylic acid with an aliphatic alcohol having 1 to 4 carbon atoms and 1 to 2 hydroxyl groups in the proportion of 0.5 – 100 moles of the aliphatic alcohol per mole of methacrylic acid, at a temperature of 160° – 360° C in the presence of a catalyst, the improvement wherein the catalyst is a solid acid silica-titania catalyst which is prepared by dissolving a silicon compound and a titanium compound in an aqueous medium in such proportions that the ratio of silicon to titanium is 0.1 – 100, adjusting the pH of the resultant aqueous solution so as to coprecipitate the silicon and the titanium components and then drying and calcining the coprecipitate to form the catalyst.

2. The process as claimed in claim 1 wherein said aliphatic alcohol is methanol or ethylene glycol.

3. The process as claimed in claim 1 wherein said silicon compound is silicon tetrachloride, a silicate salt or a silicate ester.

4. The process as claimed in claim 3 wherein said silicate salt is sodium silicate.

5. The process as claimed in claim 3 wherein said silicate ester is ethyl orthosilicate.

6. The process as claimed in claim 1 wherein said titanium compound is titanium tetrachloride, titanium sulfate or a titanate ester.

7. The process as claimed in claim 1 wherein said aqueous medium is water, a solution of a mineral acid in water, a solution of an alkali in water or a solution of an alcohol in water.

8. The process as claimed in claim 1 wherein the pH of the aqueous solution is acidic and wherein a basic substance is added to said solution to effect said pH adjustment.

9. The process as claimed in claim 1 wherein the pH of the aqueous solution is basic and wherein an acidic substance is added to said solution to effect said pH adjustment.

10. The process as claimed in claim 1 wherein said coprecipitate is calcined at a temperature of 250 – 1200° C.

11. The process as claimed in claim 1 wherein a hydroxylbearing organic compound having a molecular weight of more than 300 is dispersed in said aqueous solution.

12. The process as claimed in claim 11 wherein said hydroxylbearing organic compound is added in an amount of 1 – 100 wt% on the basis of the resultant solid silica-titania.

13. The process as claimed in claim 11 wherein said hydroxylbearing organic compound is a polysaccharide or a derivative thereof, a polymer of an unsaturated alcohol, a polyacetal or a polyalkylene glycol.

14. The process as claimed in claim 13 wherein said polysaccharide is starch or crystalline cellulose.

15. The process as claimed in claim 13 wherein said polysaccharide derivative is methyl cellulose.

16. The process as claimed in claim 13 wherein said polyalkylene glycol is polyethylene glycol having a molecular weight of more than 400.

17. The process as claimed in claim 13 wherein said polymer of the unsaturated alcohol is polyvinyl alcohol having a molecular weight of more than 500.

* * * * *